United States Patent [19]

Banks

[11] Patent Number: 4,605,810
[45] Date of Patent: Aug. 12, 1986

[54] ALLENE OR ALKYNE TREATMENT OF OLEFIN CONVERSION CATALYSTS

[75] Inventor: Robert L. Banks, Bartlesville, Okla.

[73] Assignee: Phillips Petroleum Company, Bartlesville, Okla.

[21] Appl. No.: 764,046

[22] Filed: Aug. 9, 1985

[51] Int. Cl.$^4$ .............................................. C07C 6/00
[52] U.S. Cl. .................................. 585/646; 585/600; 585/643
[58] Field of Search ............... 585/646, 643, 664, 600, 585/538, 666, 667, 671

[56] References Cited

U.S. PATENT DOCUMENTS

| | | | |
|---|---|---|---|
| 3,405,191 | 10/1968 | Banks | 585/530 |
| 3,444,262 | 5/1969 | Heckelsberg | 585/646 |
| 3,634,538 | 11/1972 | Steffgen | 585/646 |
| 3,671,462 | 6/1972 | O'Hara et al. | 585/646 |
| 3,673,114 | 6/1972 | Allum et al. | 585/646 |
| 3,725,496 | 4/1973 | Kobylinski et al. | 585/646 |
| 4,016,220 | 4/1977 | Kupper et al. | 585/643 |
| 4,024,201 | 5/1977 | Takahashi | 585/643 |
| 4,499,328 | 2/1985 | Kukes et al. | 585/646 |
| 4,504,694 | 3/1985 | Kukes et al. | 585/646 |
| 4,517,401 | 5/1985 | Kukes et al. | 585/643 |

FOREIGN PATENT DOCUMENTS

| | | | |
|---|---|---|---|
| 7307337 | 8/1973 | Netherlands | 585/643 |
| 1164687 | 9/1969 | United Kingdom | 585/646 |

Primary Examiner—Andrew H. Metz
Assistant Examiner—A. Pal
Attorney, Agent, or Firm—Stephen E. Reiter

[57] ABSTRACT

Process for activation of tungsten on silica disproportionation catalyst by contacting the catalyst with at least one acetylenic compound is disclosed. In a specific embodiment, the acetylenic compound can be prepared by isomerization of an allene compound when contacted with magnesium oxide, either as a separate catalyst bed, or as part of the disproportionation catalyst system.

11 Claims, No Drawings

4,605,810

ALLENE OR ALKYNE TREATMENT OF OLEFIN CONVERSION CATALYSTS

This invention relates to the disproportionation of olefins. In one aspect, this invention relates to the enhancement of catalyst activity of olefin disproportionation catalysts. In another aspect, this invention relates to isomerization of allenes.

BACKGROUND

The disproportionation, to metathesis, of olefins is a reaction in which one or more olefinic compounds are transformed into other olefins of different molecular weights. The disproportionation of an olefin with itself to produce an olefin of a higher molecular weight and an olefin of a lower molecular weight can also be referred to as self-disproportionation. For example, propylene can be disproportionated to ethylene and cis-, and trans-2-butene. Another type of disproportionation involves the cross-disproportionation of two different olefins to form still other olefins. An example would be the reaction of one molecule of 2-butene with one molecule of 3-hexene to produce two molecules of 2-pentene.

By the term "disproportionation" or "metathesis" throughout this specification is meant the conversion of the feed olefinic (or unsaturated) hydrocarbon to a mixture of olefinic (or unsaturated) hydrocarbons having different numbers of carbon atoms than the feed hydrocarbons.

Many catalysts have been developed for olefin disproportionation. For example, those comprising inorganic oxide supports containing a catalytic amount of metal or metal oxide have been employed widely for conversion of olefins. While many such catalysts are known, it is a continuing objective of those of skill in the art to provide catalysts with improved productivity, i.e., increased conversion of starting material and/or improved selectivity to the desired product. The present invention is based upon the discovery of a way to dramatically improve the activity of certain disproportionation catalysts.

OBJECTS OF THE INVENTION

It is, therefore, an object of the present invention to improve the activity of tungsten oxide on silica disproportionation catalysts.

This and other objects of the invention will become apparent from the disclosure and claims herein provided.

STATEMENT OF THE INVENTION

In accordance with the present invention, I have discovered that the activity of tungsten oxide on silica disproportionation catalysts is dramatically increased when contacted with at least one acetylenic compound.

In one embodiment of my invention, the tungsten oxide on silica disproportionation catalyst can be contacted with at least one acetylenic compound prior to the introduction of the olefin feed to be disproportionated, i.e., as a catalyst pretreatment.

In another embodiment of my invention, the disproportionation catalyst system can be contacted with at least one acetylenic compound intermittently throughout the disproportionation reaction by the pulsed introduction of the acetylenic compound(s) along with the olefin feed.

In yet another embodiment of my invention, where the disproportionation catalyst system includes magnesium oxide, allenic compounds can be substituted for the acetylenic compound employed for catalyst activation.

DETAILED DESCRIPTION OF THE INVENTION

In accordance with the present invention, a process for activating a tungsten oxide on silica disproportionation catalyst system is provided which comprises contacting the disproportionation catalyst system with an activating amount of at least one acetylenic compound.

In accordance with another embodiment of the invention, an improved disproportionation process is provided which comprises contacting at least one olefin with a tungsten oxide on silica disproportionation catalyst system under disproportionation conditions, the improvement comprising contacting the catalyst system with about 0.1 to 20 moles of at least one alkyne per mole of tungsten oxide.

In accordance with yet another embodiment of the invention, a method is provided for converting allenic compounds to acetylenic compounds which comprises contacting at least allene with magnesium oxide under isomerization conditions.

The tungsten oxide on silica disproportionation catalyst systems employed in the practice of the present invention consist essentially of tungsten oxide on silica support. The term "tungsten oxide on silica support" is intended to include known modifications and variations of such catalysts, including combinations such as:

$WO_3.SiO_2/R_4Sn$,
$AgO.WO_3.SiO_2$,
$OsO_4.WO_3.SiO_2$,
$WO_3.SiO_2/NbTe$,
$WO_3.SiO_2/MoTe_2$, and
$WO_3.SiO_2/MgO$.

The nomenclature employed above designates catalyst component as $X.SiO_2$ when component X is supported on the $SiO_2$, while mixed, multi-component catalyst systems are designated as $X/SiO_2$. The preparation of such catalyst systems is well known in the art and is within the capability of those of skill in the art.

Those of skill in the art recognize that the mixed, multi-component catalyst systems can be arranged so that the separate components are either employed as separate catalyst beds, with the double bond isomerization component (e.g., MgO) preceding the tungsten oxide disproportionation catalyst, or as a single bed of intimately mixed catalyst particles.

The activating agents employed in the practice of the present invention are broadly hydrocarbon compounds having acetylenic linkages. Preferred acetylenic compounds are those defined by the formula

wherein each R is independently H or a $C_1$–$C_6$ carbon radical. Examples of acetylenic compounds which conform to the above formula include ethyne, propyne, 2-butyne, 1-pentyne, 2-pentyne, 1-hexyne, 3hexyne, phenylacetylene, and the like.

In accordance with a particular embodiment of the invention, it has been discovered that allenes are isomerized to acetylenes when contacted under appropriate reaction conditions with magnesium oxide. Thus, when using a tungsten oxide disproportionation catalyst in association with magnesium oxide, allenes can optionally be employed instead of, or along with, the acetylenic compounds employed for catalyst activation. Alternatively, allenes can be fed over a bed of magnesium oxide in order to convert at least a portion of the allene feed to the isomeric acetylenic form, and such resulting acetylenic compounds can then be employed for activation of tungsten oxide on silica disproportionation catalyst.

Allenes contemplated to be useful in this embodiment of the invention are those defined by the formula:

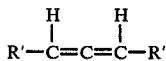

wherein each R' is independently H or a $C_1$–$C_6$ carbon radical. Examples of allenes which conform to the above formula include 1,2-propadiene, 1,2-butadiene, 1,2-pentadiene, 1,2-hexadiene, and the like.

The inventive catalyst activation procedure can be carried out in several different ways. For example, the disproportionation catalyst can be contacted with intermittent post additions of alkyne (or allene) mixed with or concurrent with the olefin feed which is undergoing disproportionation. In this way, the catalyst is further activated or "re" activated with each pulse of activating agent. Alternatively, the disproportionation catalyst system can be contacted with the acetylenic compound prior to the introduction of olefinic feed. In this way, catalyst is preactivated before commencing the disproportionation reaction. Of course, a combination of the two methodologies can be employed, such that catalyst is pretreated, then subjected to intermittent pulses over the course of an extended disproportionation reaction.

Those of skill in the art recognize that most any amount of activating agent will be effective to enhance feed conversion and/or catalyst activity. For example, when catalyst activation is carried out by the pretreatment mode, about 1 to 20 moles of alkyne (or allene) per mole of tungsten oxide are employed. When intermittent pulse addition of alkyne (or allene) is employed, pulses of generally of 0.1 mole per mole of tungsten oxide and usually not exceeding about 20 moles per mole of tungsten oxide are employed. There is no limit as to the number of pulses of activating agent which can beneficially be employed, as each addition will be expected to cause enhanced catalyst performance. Thus, there is no limit as to the total quantity of activating agent employed. Regardless of the mode of activating treatment employed, in accordance with the present invention, catalyst is contacted with the activating agent at disproportionation reaction conditions.

Catalysts activated according to the invention are useful, for example, for the conversion of olefins via the olefin disproportionation or olefin metathesis reaction.

REACTANTS

The process of the present invention comprises contacting at least one olefin selected from the group consisting of acyclic mono- and polyenes having at least three up to 10 carbon atoms per molecule and cycloalkyl and aryl derivatives thereof; cyclic mono- and polyenes having at least four up to 10 carbon atoms per molecule and alkyl and aryl derivatives thereof; mixtures of two or more of the above olefins; and mixtures of ethylene with one or more of the above olefins capable of undergoing disproportionation with catalysts prepared according to the invention. Where mixtures of the above olefins with ethylene are subjected to disproportionation reaction conditions, it is desirable that the molar ratio of ethylene to olefin be at least 2. Preferably, ethylene:olefin ratios of about 4:1 or higher will be employed for good results.

Some specific examples of olefins suitable for reactions of this invention include propylene, 1-butene, 2-butene, 1-pentene, 2-pentene, 2,4,4-trimethyl-2-pentene and 2,4,4-trimethyl-1-pentene (diisobutylene isomers), 1-hexene, 1,4-hexadiene, 2-heptene, 1-octene, 2,5-octadiene, 2-nonene, 1-decene, 1-phenyl-2-butene, 4-octene, 3-hexene, vinylcyclohexane, 1,4-pentadiene, 2-methyl-4-octene, 4-vinylcyclohexene, 1,7-octadiene, 6,6-dimethyl-1,4-octadiene, and 3-heptene, and the like, and mixtures of two or more thereof.

Some specific examples of cyclic olefins suitable for the reactions of this invention are cyclobutene, cyclopentene, cycloheptene, cyclooctene, 5-n-propylcyclooctene, cyclodecene, 1,5-cyclooctadiene, 1,5,9-cyclodecatriene, and the like, and mixtures of two or more thereof.

DISPROPORTIONATION REACTION CONDITIONS

The reaction temperature can vary depending upon the catalyst(s) and feed(s) employed and upon the desired reaction products. Typically the disproportionation reaction is carried out at a temperature in the range of about 0° to about 600° C.; preferably for good conversion in relatively short reaction times, temperatures of from about 20 to about 500° C. are employed.

The disproportionation reaction can be carried out by contacting the olefins to be disproportionated with the catalyst system in the liquid phase or the gas phase depending on the structure and molecular weight of the olefin. Pressure during the disproportionation reaction can vary between wide limits. For example, pressures between 0.1 and 500 atmospheres are suitable, although preferred pressures are between about 1 and 40 atmospheres because good conversions are obtained with readily available equipment.

If the reaction is carried out in the liquid phase, solvents or diluents for the reactants can be used. Aliphatic saturated hydrocarbons e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, propane, and/or substantially inert gases, e.g. nitrogen, argon, can be present. Preferably, for high product yield, the disproportionation reaction is effected in the absence of significant amounts of deactivating materials such as water and oxygen.

The contact time needed to obtain a reasonable yield of disproportionation products depends upon several factors such as the activity of the catalyst, temperature, pressure and structure of the olefinically unsaturated compound(s) to be disproportionated. Length of time during which the olefinic unsaturated compounds to be disproportionated are contacted with the catalyst can conveniently vary between 0.1 seconds and 24 hours although longer and shorter contact times can be used. Preferably, for efficient use of reactor equipment, times of about 1 second to about 1 hour are used.

The process of the invention can be effected batchwise or continuously with fixed catalyst beds, slurried catalyst, fluidized beds, or by using any other conventional contacting techniques.

ALLENE ISOMERIZATION CONDITIONS

Reaction conditions employed for the isomerization of allenes to alkynes can vary widely. Typically an isomerization temperature in the range of about 25° to 600° C., at a pressure in the range of about 0.1 to 500 atm, with contact times in the range of 0.1 seconds up to about 24 hours. It is understood by those of skill in the art that longer contact times will be employed at lower reaction temperatures, while shorter contact times will be employed at higher reaction temperatures. Preferred parameters are a temperature in the range of about 200°–500° C. at a pressure in the range of about 1 to 40 atmospheres with contact times in the range of about 1 second to about 1 hour.

PRODUCTS

The olefinic products of the invention have established utility including use as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form polyamides which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following non-limiting examples.

EXAMPLE I

This example describes the experimental procedure used in the present work.

I. Catalysts

(a) $WO_3.SiO_2$ Catalyst

The supported tungsten oxide component of the $WO_3.SiO_2$ disproportionation catalyst system was about 6 weight percent metal oxide based on the total weight of tungsten oxide and silica. Impregnation was accomplished by treating the silica with an aqueous solution of ammonium metatungstate $[(NH_4)_2W_4O_{13}.8H_2O]$. The impregnated silica was oven dried and then calcined in air at 500° C. to convert the metal compounds to the oxide form. Fractions passing −20 to +40 mesh sieves were separated for use in the experimental runs. These fractions were suitable for activation and evaluation in conventional reactor vessels under metathesis conditions.

In a typical run, about 0.75 g of $WO_3.SiO_2$ (ca. 6 wt % $WO_3$) was used in the metathesis reactor.

(b) $MgO/WO_3.SiO_2$ Catalyst

The supported tungsten oxide on silica disproportionation catalyst, prepared as described in (a), was preceded by a layer of magnesium oxide. The MgO and $WO_3.SiO_2$ layers can be in contact or separated by a void space in the reactor.

In a typical run with the $MgO/WO_3.SiO_2$ layered catayst, 1.5 g of MgO and 0.75 g $WO_3.SiO_2$ was used.

(c) Mixed $MgO+WO_3.SiO_2$ Catalyst

The supported tungsten oxide on silica disproportionation catalyst, prepared as described in (a), was mixed with MgO.

In a typical run with the mixed magnesium oxide tungsten-oxide-on-silica catalyst, 1.5 g of MgO was intimately mixed with 0.75 g $WO_3.SiO_2$.

II. Catalyst Activation

In each run, the supported tungsten oxide catalyst was activated in air at 600° C. for about 75 minutes, maintained at 600° C. for 15 minutes under a nitrogen flow, then optionally treated with carbon monoxide for 15 minutes at 600° C. and finally purged with nitrogen for 15 minutes at 600° C. before allowing the catalyst bed to cool to the desired reaction temperature under a nitrogen flow.

III. Test Run Procedure

All runs were made by passing a propylene feed through a vertical tubular quartz reactor (1 cm in diameter and 25 cm in length) positioned in a temperature-controlled electric furnace. In each run the reactor contained a bed of $WO_3.SiO_2$ or a mixed bed of MgO and $WO_3.SiO_2$. Preferably, MgO preceded the $WO_3.SiO_2$ disproportionation catalyst. A thermocouple was positioned in the catalyst bed to monitor reaction temperature. Prior to each run, the catalyst was treated at 600° C. in flowing nitrogen for 15–30 minutes.

Catalyst regeneration was accomplished with flowing air at 600° C. for 15 to 60 minutes followed by a nitrogen flush at 600° C. for about 15 minutes, optional carbon monoxide flow for 15 minutes at 600° C. then nitrogen flush to cool the catalyst to the desired reaction temperature.

IV. Olefin Feed and Product Analyses

The propylene feed was of a polymerization grade as sold by Phillips Petroleum Co. of Bartlesville, Okla. The propylene feed was pretreated with activated Alcoa H151 alumina and activated magnesia prior to the metathesis runs. The feed was passed downwardly through the vertically oriented tubular reactor and reaction product analyses were made by gas-liquid chromatography (glc) employing a Hewlett-Packard model 5880A chromatograph having a ⅛ inch by 20 ft. column packed with 19% bis-2-methoxyethoxyethylene (BMEE) +1% squalene on 60/80 Chrom P. Analysis was carried out isothermally at a temperature of about 30° C. to 40° C. with a helium carrier gas flow rate of about 20 mL/min.

V. Pulsed Additions of Alkynes and Alkyne Precursors

A conventional glc sample valve installed in the reactor inlet line was used to add controlled size pulses of gaseous alkynes into the system. Liquid alkynes were syringe-injected into the top of the reactor. The alkynes were obtained from commercial chemical suppliers and were used without purification. In one embodiment, the pulsed addition of alkynes preceded the introduction of olefin feed, i.e. at reaction time zero.

Alkyne precursors such as allene were also found to be suitable activating agents in the instant process provided that the layered $MgO/WO_3.SiO_2$ catalyst was used. As shown hereinbelow, the allene on contacting the MgO layer is isomerized to methylacetylene (propyne) within the reactor resulting in the enhancement of propylene conversion. The allene obtained from a commercial chemical supplier was used without further purification. The allene was syringe-injected into the top of the reactor.

EXAMPLE II

This example describes inventive runs carried out over the $WO_3.SiO_2$ catalyst system. The following alkynes were found suitable for enhancing propylene conversion: acetylene, propyne, 2-butyne, 1-pentyne, 2-pentyne, 1-hexyne, 3-hexyne and phenylacetylene. Results are summarized in Tables I-XI. In some of the runs, the alkyne was pulsed into the reactor before the injection of the propylene feed, i.e., at reaction time zero.

TABLE I

Acetylene Pulses To Enhance Propylene Conversion Over $WO_3.SiO_2$ @ 400° C.

| Run No. | Total Minutes on Stream | Injected Pulses of Acetylene @ Minutes on Stream | % Propylene Conversion |
|---|---|---|---|
| 1[a] | 5 | | 1.2 |
| | 25 | | 5.4 |
| | 46 | | 7.4 |
| | | 55 | |
| | 66 | | 8.5 |
| | | 86 | |
| | 87 | | 40.9 |
| | 107 | | 34 |
| | 128 | | 31.3 |
| | 148 | | 29.7 |
| | 169 | | 28.9 |
| | 189 | | 28.2 |
| | | 210 | |
| | 210 | | 23.9 |
| | 243 | | 38.9 |
| | 264 | | 37 |

[a]CO Activated catalyst

Referring to the results in run 1 of Table I, it is evident that pulses of acetylene caused increased propylene conversion. For example, pulses of acetylene at 86 and 210 minutes caused significant increases in propylene conversion, respectively, in samples withdrawn for analysis at 87 minutes and 243 minutes.

TABLE II

Acetylene Pulsed to the Reactor Before Propylene Feed for Enhancing Propylene Conversion Over $WO_3.SiO_2$ @ 400° C.

| Run No. | Total Minutes on Stream | Injected Pulses of Acetylene @ Minutes on Stream | % Propylene Conversion |
|---|---|---|---|
| 2* | 0 | 0 | 0 |
| | 5 | | 3.3 |
| | 25 | | 18.3 |
| | 46 | | 24.1 |
| | 66 | | 27.3 |
| | 87 | | 29 |
| | 108 | | 30.3 |
| | | 126 | |
| | 128 | | 42.1 |
| | 149 | | 39.2 |

*Catalyst was not activated with CO; the initial pulse of acetylene into the reactor at 600° C. preceded the introduction of propylene into the reactor.

Referring to the results in run 2 of Table II, it is evident that pulsing of acetylene to the reactor before the introduction of any propylene feed gave a higher propylene conversion, i.e., after 25 minutes, a conversion of 18.3% was observed, while a conversion of only 5.4%@25 minutes was observed in run 1, wherein the initial pulse of acetylene was not introduced until the system had been on stream for 55 minutes. Run 2 of Table II exhibited a shorter induction period than did run 1 of Table I.

TABLE III

Propyne Pulses to Enhance Propylene Conversion Over $WO_3.SiO_2$ @ 400° C.

| Run No. | Total Minutes on Stream | Injected Pulses of Propyne @ Minutes on Stream | % Propylene Conversion |
|---|---|---|---|
| 3[a] | 5 | | 5.2 |
| | 25 | | 14 |
| | 46 | | 18 |
| | 66 | | 20.8 |
| | 87 | | 23.3 |
| | | 96 | |
| | 107 | | 21.3 |
| | 128 | | 22.5 |
| | 148 | | 24.4 |
| | | 159 | |
| | 169 | | 29.4 |
| | 189 | | 27.9 |
| | | 201 | |
| | 210 | | 42.3 |
| | 230 | | 40.2 |
| | 251 | | 39 |
| | 271 | | 38.6 |

[a]Catalyst activated with CO.

Referring to the results in run 3 of Table III, it is evident that pulses of propyne (methylacetylene) caused increased propylene conversion. For example, pulses of propyne at 159 and 201 minutes caused significant increases in propylene conversion, respectively, in samples withdrawn for analysis at 169 minutes and 210 minutes.

TABLE IV

2-Butyne Pulses To Enhance Propylene Conversion Over $WO_3.SiO_2$

| Run No. | Total Minutes on Stream | Injected Pulses of 2-Butyne @ Minutes on Stream | % Propylene Conversion |
|---|---|---|---|
| 4[a] | 5 | | 3.2 |
| | 25 | | 6.7 |
| | 46 | | 9 |
| | | 52 | |
| | 66 | | 43.5 |
| | 87 | | 42.8 |
| | | 107 | |
| | 107 | | 3.3 |
| | 128 | | 43.4 |
| | 149 | | 42.9 |
| 5[b] | 46 | 49 | 0.1 |
| | 57 | | 40.5 |
| | 77 | | 36.5 |
| 6[c] | 79 | | |
| | 97 | | 4.2 |
| | | 104 | |
| 6[c] | 117 | | 2.7 |
| | | 125 | |
| | 138 | | 19.6 |
| | 154 | | 21.8 |

[a]CO activated catalyst; run temperature 400° C.
[b]Run temperature 300° C.
[c]Run temperature reduced to 200° C.

Referring to the results of runs 4, 5 and 6 in Table IV, it is evident that pulses of 2-butyne caused enhanced propylene conversions, respectively, at reactor temperatures of 400° C., 300° C. and 200° C. In the 400° C. test (run 4) pulses of 2-butyne at 52 and 107 minutes caused sharp increases in propylene conversion, respectively, at 66 and 128 minutes. The very low conversion of 3.3% recorded at 107 minutes is a typical minimum frequently noted after each injected alkyne pulse followed by a sharp increase in conversion. In the 300° C. test (run 5) a pulse of 2-butyne at 49 minutes caused a sharp increase in propylene conversion at 57 minutes. Similarly in run 6, pulses of 2-butyne at 104 and 125 minutes caused a sharp increase in propylene conversion at 138 minutes.

TABLE V

2-Butyne Pulsed To The Reactor Before Propylene Feed For Enhancing Propylene Conversion Over $WO_3.SiO_2$ @ 400° C.

| Run No. | Total Minutes on Stream | Injected Pulses of 2-Butyne @ Minutes on Stream | % Propylene Conversion |
|---|---|---|---|
| 7* | 0 | 0 | 0 |
|  | 5 |  | 36.5 |
|  | 25 |  | 35.7 |
|  | 46 |  | 33.5 |
|  | 66 |  | 31.4 |
|  | 87 |  | 29.3 |
|  | 107 |  | 27.8 |
|  |  | 108 |  |
|  | 128 |  | 41.8 |

*Catalyst was not activated with CO; the initial pulse of 2-butyne into the reactor at 400° C. preceded the introduction of propylene into the reactor.

Referring to the results in run 7 of Table V, it is evident that pulsing of 2-butyne to the reactor before the introduction of propylene feed gave a higher propylene conversion after 5 minutes, i.e., 36.5%, than was observed in run 4 of the Table IV (3.2% @ 5 minutes) wherein the initial pulse of 2-butyne was not introduced until the system had been on stream for 52 minutes. Run 7 of Table V exhibited a shorter induction period than did run 4 of Table IV.

TABLE VI

1-Pentyne Pulses To Enhance Propylene Conversion Over $WO_3.SiO_2$ @ 400° C.

| Run No. | Total Minutes on Stream | Injected Pulses of 1-Pentyne @ Minutes on Stream | % Propylene Conversion |
|---|---|---|---|
| 8[a] | 5 |  | 6.3 |
|  | 25 |  | 11.6 |
|  | 45 |  | 14.7 |
|  |  | 50 |  |
|  | 65 |  | 25.7 |
|  | 86 |  | 23.5 |
|  | 106 |  | 22.4 |
|  |  | 126 |  |
|  | 127 |  | 4 |
|  | 148 |  | 35.2 |
|  | 169 |  | 34.1 |
|  | 189 |  | 32.6 |

[a]CO activated catalyst.

Referring to the results in run 8 of Table VI, it is evident that 1-pentyne pulses caused increased propylene conversions. For example, pulses of 1-pentyne at 50 and 126 minutes caused dramatic increases in propylene conversion, respectively, at 65 and 148 minutes. The very low conversion of 4% recorded at 127 minutes was characteristic of the process wherein the system generally exhibited a minimum in propylene conversion immediately after an alkyne pulse followed shortly thereafter by a sharp increase in conversion.

TABLE VII

Pentynes Pulses to the Reactor Before Propylene Feed For Enhancing Propylene Conversion Over $WO^a SiO_2$ @ 400° C.

| Run No. | Total Minutes on Stream | Injected Pulses of Additive @ Minutes on Stream | % Propylene Conversion |
|---|---|---|---|
| 9[a] | 0 | 0* | 0 |
|  | 5 |  | 36.8 |
|  | 25 |  | 26.5 |
|  | 46 |  | 20.5 |
|  |  | 51 |  |
|  | 66 |  | 40 |
|  | 87 |  | 33.7 |
|  | 107 |  | 26.5 |
|  |  | 126 |  |
|  | 128 |  | 41.5 |
| 10[b] | 0 | 0** | 0 |
|  | 5 |  | 11.3 |
|  | 25 |  | 12.2 |
|  | 46 |  | 13.2 |
|  |  | 50 |  |
|  | 66 |  | 20.2 |
|  | 87 |  | 18.2 |

*2-Pentyne pulse was added before propylene was fed to the reactor. A 10 wt % solution of 2-pentyne in cyclohexane was used (Run 9).
**1-Pentyne pulse was added before propylene was fed to the reactor. A 10 wt % solution of 1-pentyne in cyclohexane was used (Run 10).
[a]Catalyst was not activated with CO.
[b]The catalyst of run 9 was regenerated as known in the art and not activated with CO.

Referring to the results of runs 9 and 10 in Table VII, it is evident that pulses of 2-pentyne caused more dramatic increases in propylene conversion than did a pulse of 1-pentyne. For example, in run 9, pulses of 2-pentyne (as a 10 wt % solution in cyclohexane) at 51 and 126 minutes caused sharp increases in propylene conversion, respectively, at 66 and 128 minutes. The initially high conversion of 36.8% at 5 minutes in run 9 resulted from the introduction of a pulse of 2-pentyne into the reactor before feeding propylene to the reactor.

Run 10 demonstrates that 1-pentyne was less effective than 2-pentyne in regard to enhancing propylene conversion level. The conversion level at 5 minutes was only 11.3% compared to 36.8% noted above. A pulse of 1-pentyne injected at 50 minutes increased propylene conversion to 20.2 at 66 minutes compared to the 40+% conversion levels recorded in the 2-pentyne system (run 9).

TABLE VIII

1-Hexyne Pulses To Enhance Propylene Conversion Over $WO_3.SiO_2$ @ 400° C.

| Run No. | Total Minutes on Stream | Injected Pulses of 1-Hexyne @ Minutes on Stream | % Propylene Conversion |
|---|---|---|---|
| 11[a] | 5 |  | 2.4 |
|  | 25 |  | 5.7 |
|  | 45 |  | 7.8 |
|  |  | 50 |  |
|  | 66 |  | 30.5 |
|  | 86 |  | 26.3 |
|  | 107 |  | 26.5 |
|  | 127 |  | 24.8 |
|  | 148 |  | 23.9 |
|  |  | 167 |  |
|  | 168 |  | 1.9 |
|  | 189 |  | 36.2 |
|  | 209 |  | 34.5 |
|  | 230 |  | 33 |
|  | 250 |  | 31.6 |

[a]CO activated catalyst.

Referring to the results in run 11 of Table VIII, it is evident that 1-hexyne pulses caused increased propylene conversions. For example, pulses of 1-hexyne at 50 and 167 minutes caused dramatic increases in propylene conversion, respectively, at 66 and 189 minutes. The very low conversion of 1.9% recorded at 168 minutes was characteristic of the process wherein the system generally exhibited a momentary minimum in propylene conversion immediately after an alkyne pulse followed shortly thereafter by a sharp increase in conversion.

TABLE IX

Dosage Levels of 1-Hexyne Pulsed to the Reactor Before Propylene Feed For Enhancing Propylene Conversion Over $WO_3.SiO_2$ @ 400° C.

| Run No. | Total Minutes on Stream | Injected Pulses of 1-hexyne @ minutes on Stream | Wt (gm) | % Propylene Conversion |
|---|---|---|---|---|
| 12[a] | 0 | 0 | 0.02 | 0 |
| | 5 | | | 4.4 |
| | 25 | | | 13.1 |
| | 46 | | | 16.6 |
| | 66 | | | 19.1 |
| 13[b] | 0 | 0 | 0.11 | 0 |
| | 6 | | | 29.5 |
| | 27 | | | 27.6 |
| | 48 | | | 27.2 |
| | 68 | | | 27.5 |
| | 89 | | | 27.4 |
| 14[c] | 0 | 0 | 0.19 | 0 |
| | 5 | | | 27.8 |
| | 25 | | | 27.9 |
| | 45 | | | 28.1 |

[a]Catalyst was not activated with CO; the designated quantities of 1-hexyne were introduced into the reactor at 400° C. before the introduction of any propylene feed into the reactor.
[b,c]Catalyst of run 12 was regenerated sequentially for runs 13 and 14.

Referring to the results in runs 12, 13 and 14 in Table IX, it is evident that dosages of greater than 0.02 g 1-hexyne per 0.75 g $WO_3.SiO_2$ are required to give the shortened induction period for propylene conversion. For example, in run 12 (0.02 g 1-hexyne) the % propylene conversion at 5 minutes was 4.4 whereas in runs 13 (0.11 g 1-hexyne) and 14 (0.19 g 1-hexyne) the % propylene conversion, respectively, at 6 minutes and 5 minutes on stream were 29.5% and 27.8%.

TABLE X

3-Hexyne Pulses to Enhance Propylene Conversion Over $WO_3.SiO_2$ @ 400° C.

| Run No. | Total Minutes on Stream | Injected Pulses of 3-Hexyne @ Minutes on Stream | % Propylene Conversion |
|---|---|---|---|
| 15[a] | 5 | | 1.2 |
| | 25 | | 6.2 |
| | 46 | | 8.8 |
| | | 52 | |
| | 66 | | 41.4 |
| | 87 | | 41.2 |
| | | 106 | |
| | 107 | | 2.6 |
| | 128 | | 42.2 |
| | 148 | | 40.9 |

[a]CO activated catalyst.

Referring to the results in run 15 of Table X it is evident that 3-hexyne pulses caused increased propylene conversions. For example, pulses of 3-hexyne at 52 and 106 minutes caused dramatic increases in propylene conversion, respectively, at 66 and 128 minutes. The very low connversion of 2.6% recorded at 107 minutes was characteristic of the process wherein the immediate response of the system to an alkyne pulse was a momentary minimum in propylene conversion followed shortly thereafter by a sharp increase in conversion.

TABLE XI

Phenylacetylene Pulses To Enhance Propylene Conversion Over $WO_3.SiO_2$ @ 400

| Run No. | Total Minutes on Stream | Injected Pulses of $C_6H_5C \equiv CH$ @ Minutes on Stream | % Propylene Conversion |
|---|---|---|---|
| 16[a] | 46 | | 7.2 |
| | | 56 | |
| | 66 | | 30.5 |
| | | 86 | |
| | 87 | | 38.9 |
| | | 127 | |
| | 128 | | 0.9 |
| | 149 | | 41.7 |
| | 169 | | 34.4 |
| 17[c] | 5[d] | | 36.2 |
| | 25 | | 25.1 |
| | 46 | | 24.2 |
| | 66 | | 24.2 |
| | | 77 | |
| | 87 | | 43.0 |
| | 107 | | 42.0 |

[a]CO activated catalyst.
[b]A 20 wt % solution of $C_6H_5C \equiv CH$ in cyclohexane was used.
[c]No CO activation of the catalyst.
[d]A 0.09 g sample of $C_6H_5C \equiv CH$ (neat) was injected 1 minute before the propylene feed was started.

Referring to the results in run 16 of Table XI, it is evident that the pulses of phenylacetylene caused enhanced propylene conversions. For example, in run 16, pulses of $C_6H_5C \equiv CH$ at 56, 86 and 127 minutes caused dramatic increases in propylene conversion, respectively, at 66, 87 and 149 minutes. The very low conversion of 0.9% recorded at 128 minutes was characteristic of the process in that the temporary response to an alkyne pulse injection was a momentary minimum in propylene conversion followed by a sharp increase in conversion.

Comparing the results of run 16 and run 17 of Table XI, it is evident in run 17 that the pulse of $C_6H_5C \equiv CH$ injected into the reactor before any propylene feed was introduced caused a much higher conversion, i.e., 36.2% at 5 minutes on stream compared to 7.2% conversion at 46 minutes in run 17. The subsequent pulse of phenylacetylene at 77 minutes on stream caused the % conversion to increase from 24.2@ 66 minutes to 43.0@ 87 minutes.

EXAMPLE III

This example describes inventive runs carried out over the layered $MgO/WO_3.SiO_2$ system wherein the respective beds of MgO and $WO_3.SiO_2$ can be in contact or said beds can be separated by a void space in the vertical reactor. The MgO bed is always above the $WO_3.SiO_2$ bed. The following alkynes were found suitable for increasing propylene conversion: acetylene, propyne, 2-pentyne and 1-hexyne. Results are summarized in Tables XII–XV.

This example also describes inventive runs in which allene is added to increase propylene conversion. In these runs it is necessary that the allene be passed through the MgO bed first. This technique results in the isomerization of the allene to propyne which is the active agent for enhancing propylene conversion. Results for an inventive allene run are summarized in Table XVI. The ineffectiveness of allene pulses on the $WO_3.SiO_2$ catalyst (no MgO present) is substantiated by the summary of results in Table XVII. The effectiveness of MgO as a catalyst for isomerization of allene to propyne is substantiated by the summary of results to Table XVI.

TABLE XII

Acetylene Pulses To Enhance Propylene Conversion Over Layered MgO/WO$_3$.SiO$_2$ Catalyst @ 275° C.

| Run No. | Total Minutes on Stream | Injected Pulses of Acetylene @ Minutes on Stream | % Propylene Conversion |
|---|---|---|---|
| 18[a] | 5 | | 23.4 |
| | 25 | | 24.2 |
| | 46 | | 22.7 |
| | 66 | | 21.7 |
| | 87 | | 21.3 |
| | 107 | | 21.5 |
| | | 127 | |
| | 130 | | 40.6 |
| | 151 | | 36.8 |
| | 171 | | 36.4 |
| | | 191 | |
| | 192 | | 41.4 |
| | 212 | | 36.6 |
| | 233 | | 36.8 |

[a]CO activated catalyst.

Referring to the results of run 18 in Table XII, it is evident that acetylene pulses through the layered MgO/WO$_3$.SiO$_2$ catalyst caused increased propylene conversions. For example, pulses of acetylene at 127 and 191 minutes caused significant increases in propylene conversion, respectively, at 130 and 192 minutes.

TABLE XIII

Propyne Pulses To Enhance Propylene Conversion Over Layered MgO/WO$_3$.SiO$_2$ Catalyst @ 300° C.

| Run No. | Total Minutes on Stream | Injected Pulses of Propyne @ Minutes on Stream | % Propylene Conversion |
|---|---|---|---|
| 19[a] | 5 | | 34.2 |
| | 25 | | 33 |
| | 46 | | 38.4 |
| | | 65 | |
| | 66 | | 33.8 |
| | 87 | | 12.1 |
| | 108 | | 40.3 |
| | 128 | | 40.1 |
| | | 150 | |
| | 152 | | 0.5 |
| | 177 | | 31.1 |

[a]CO activated catalyst.

Referring to the results in run 19 of Table XIII, it is evident that a pulse of propyne through the layered MgO/WO$_3$.SiO2 catalyst caused a significant increase in propylene conversion. A pulse of propyne at 65 minutes resulted in a significant increase in propylene conversion at 108 minutes. A pulse of propyne at 150 minutes resulted in the typical momentary minimum in propylene conversion at 152 minutes before the propylene % conversion reestablished itself at higher levels.

TABLE XIV

2-Pentyne Pulses To Enhance Propylene Conversion Over Layered MgO/WO$_3$.SiO$_2$ Catalyst @ 300° C.

| Run No. | Total Minutes of Stream | Injected Pulses of 2-Pentyne @ Minutes on Stream | % Propylene Conversion |
|---|---|---|---|
| 20[a] | 5 | | 1.9 |
| | 25 | | 4.7 |
| | | 34 | |
| | 46 | | 31.2 |
| | 66 | | 22.2 |
| | 87 | | 19.1 |
| | 107 | | 17.6 |
| | 128 | | 16.5 |
| | | 143 | |
| | 148 | | 26.2 |
| | 169 | | 18.4 |

[a]CO activated catalyst.

Referring to the results of run 20 in Table XIV, it is evident that 2-pentyne pulses through the layered MgO/WO$_3$.SiO$_2$ catalyst caused increased propylene conversions. For example, pulses of 2-pentyne at 34 and 143 minutes caused significant increases in propylene conversion, respectively, at 46 and 148 minutes.

TABLE XV

1-Hexyne Pulses To Enhance Propylene Conversion Over Layered MgO/WO$_3$.SiO$_2$ Catalyst @ 275° C.

| Run No. | Total Minutes on Stream | Injected Pulses of 1-Hexyne @ Minutes on Stream | % Propylene Conversion |
|---|---|---|---|
| 21[a] | 5 | | 26 |
| | 5 | | 26 |
| | 46 | | 23.5 |
| | | 56 | |
| | 66 | | 42 |
| | 87 | | 41.8 |
| | | 97 | |
| | 107 | | 42.2 |
| | 128 | | 41.8 |
| | 149 | | 41.7 |
| | 169 | | 41.3 |
| | 190 | | 41.1 |

[a]CO activated catalyst.

Referring to the results in run 21 of Table XV, it is evident that a pulse of 1-hexyne through the layered MgO/WO$_3$.SiO$_2$ catalyst resulted in increased propylene conversion. A pulse of 1-hexyne at 56 minutes resulted in a dramatic increase in the % propylene conversion at 66 minutes. A subsequent pulse of 1-hexyne at 97 minutes caused no sharp increase in propylene conversion, since this conversion level is essentially equilibrium at this reaction temperature, but probably aided in maintaining the conversion at about 41% during the remainder of the run.

TABLE XVI

Allene Pulses Through the Layered MgO/WO$_3$.SiO$_2$ Catalyst To Enhance Propylene Conversion in Metathesis @ 300° C.

| Run No. | Total Minutes on Stream | Injected Pulses of Allene @ Minutes on Stream | % Propylene Conversion |
|---|---|---|---|
| 22[a] | 87 | | 23.2 |
| | 107 | | 25.8 |
| | 128 | | 27.5 |
| | 148 | | 28.8 |
| | 169 | | 29.9 |
| | 189 | | 30.8 |
| | | 196 | |
| | 210 | | 41.9 |
| | 230 | | 41.9 |
| | 251 | | 40.7 |
| | 256** | | |
| | 271 | | 15.9 |
| | 280* | | |
| | 292 | | 27 |
| | | 296 | |
| | 312 | | 42 |
| | 333 | | 41.4 |
| | 354 | | 40.3 |
| | | 372 | |
| | 374 | | 0.4 |

TABLE XVI-continued

Allene Pulses Through the Layered MgO/WO$_3$.SiO$_2$ Catalyst
To Enhance Propylene Conversion in Metathesis @ 300° C.

| Run No. | Total Minutes on Stream | Injected Pulses of Allene @ Minutes on Stream | % Propylene Conversion |
|---|---|---|---|
| | 395 | | 44.2 |

$^a$CO activated catalyst.
*All of the propylene feed was introduced through the MgO bed.
**20% of the propylene was introduced downstream of the MgO layer.

Referring to the results of run 22 in Table XVI, it is evident that the passage of allene through the layered MgO/WO$_3$.SiO$_2$ catalyst bed caused significant increases in propylene conversion. For example, pulses of allene at 196, 296 and 372 minutes resulted in dramatic increases in % propylene conversion, respectively, at 210, 312 and 395 minutes. The minimum in % propylene conversion immediately following the allene pulse at 372 minutes was characteristic of many experimental runs: generally this minimum was soon followed by the typical enhancement in propylene conversion.

In a separate experiment, a sample of allene was passed through a bed of MgO only @ 300° C. and glc analysis of the effluent showed an 82% conversion of allene with a 90% selectivity to propyne (methylacetylene). A similar run with propylene feed @ 300° C. showed no detectable propyne (methylacetylene) in the glc analysis of the reactor effluent. A similar result was obtained by passing propylene through MgO @ 400° C. A final run @ 500° C. showed 0.014% propyne in the reactor effluent (glc analysis). In each of these runs the MgO bed was conditioned in the same manner as was the layered MgO/WO$_3$.SiO$_2$ catalyst used in Example III.

TABLE XVII

Allene Pulses to the WO$_3$.SiO$_2$ Catalyst
To Enhance Propylene Conversion in Metathesis @ 400° C.

| Run No. | Total Minutes on Stream | Injected Pulses of Allene @ Minutes on Stream | % Propylene Conversion |
|---|---|---|---|
| 23$^a$ | 107 | | 20.2 |
| | 128 | | 21.8 |
| | 148 | | 23.1 |
| | 169 | | 24.2 |
| | 189 | | 25.2 |
| | 210 | | 25.9 |
| | 230 | | 26.8 |
| | | 239* | |
| | 251 | | 24.2 |
| | 271 | | 26 |
| | 292 | | 27.4 |
| | | 305* | |
| | 312 | | 22.9 |
| | 333 | | 26 |
| | 353 | | 28.1 |
| | | 372** | |
| | 374 | | 36.5 |
| | 394 | | 37.2 |

$^a$CO activated catalyst.
*5 mL pulse of allene.
**5 mL pulse of propyne.

Referring to the results in run 23 of Table XVII, it is evident that allene pulses to the WO$_3$.SiO$_2$ catalyst (containing no MgO) did not cause significant changes in the % propylene conversion. Presumably this behavior was observed because the required isomerization of allene to methylacetylene (an alkyne) did not occur in the absence of the MgO component. It is noteworthy that the pulsing of propyne (methylacetylene, an alkyne) at 372 minutes caused a significantly increased propylene conversion as observed by analysis of the sample taken at 374 minutes.

EXAMPLE IV

This example describes comparison runs in which selected hydrocarbons containing multiple bonds as well as other selected materials containing multiple bonds failed to enhance propylene conversion over typical olefin metathesis catalysts such as WO$_3$.SiO$_2$ and layered MgO/WO$_3$.SiO$_2$. Pulses of the following materials were investigated: 1,3-butadiene; nitrogen and acetonitrile. The results of these runs are summarized in Tables XVIII–XX.

TABLE XVIII

Effect 1,3-Butadiene and Nitrogen Cofeeds on Propylene
Conversion Over WO$_3$.SiO$_2$ @ 400° C.

| Run No. | Total Minutes on Stream | Injected Additive @ Minutes on Stream | % Propylene Conversion |
|---|---|---|---|
| 24$^a$ | 66 | | 23 |
| | 87 | | 26.2 |
| | 107 | | 28.9 |
| | 128 | | 31.2 |
| | 148 | | 32.9 |
| | | 154 (N$_2$)* flow on | |
| | 169 | | 4.4 |
| | 189 | | 5.4 |
| | | 189 (N$_2$)** | |
| | 210 | | 24.5 |
| | 218 | (N$_2$)** flow off | |
| | 230 | | 29.3 |
| | | 239$^b$ flow on | |
| | 251 | | 1.1 |
| | 257$^b$ | flow off | |
| | 271 | | 5.1 |
| | 291 | | 5.0 |

$^a$CO activated catalyst.
$^b$1,3-Butadiene pulse through MgO and then WO$_3$.SiO$_2$.
*N$_2$ introduced downstream of the MgO layer.
**N$_2$ introduced through MgO and then through WO$_3$.SiO$_2$.

Referring to the results in run 24 of Table XVIII, it is evident that the addition of either CH$_2$=CH—CH=CH$_2$ (1,3-butadiene) or elemental nitrogen (N≡N) through the layered MgO/WO$_3$.SiO$_2$ catalyst resulted in no dramatic increase in propylene conversion in a typical propylene metathesis operation. A flow of N$_2$ amounting to 5–15% of the injected feed downstream of the MgO layer at 154 minutes resulted in very low levels of propylene conversion at 169 and 189 minutes. A flow of N$_2$ amounting to 5% of the injected feed through both the MgO and WO$_3$.SiO$_2$ layers appeared to have had no effect as the propylene conversion returned to the level observed prior to any injection of N$_2$. By contrast, the introduction of 1,3-butadiene beginning at 239 minutes and continuing until 257 minutes, caused the propylene conversion to drop to very low levels in the range of about 1%, which increased to about 5% when butadiene introduction was discontinued to 5%.

TABLE XIX 1,3-Butadiene Pulses to WO$_3$.SiO$_2$ Catalyst
To Enhance Propylene Conversion in Metathesis @ 400° C.

| Run No. | Total Minutes on Stream | Injected Pulses of 1,3-Butadiene @ Minutes on Stream | % Propylene Conversion |
|---|---|---|---|
| 25$^a$ | 5 | | 4.7 |
| | 25 | | 9.9 |
| | 46 | | 12.7 |
| | 66 | | 15.2 |
| | 87 | | 16.9 |
| | 107 | | 18.5 |

TABLE XIX-continued 1,3-Butadiene Pulses to WO$_3$.SiO$_2$ Catalyst
To Enhance Propylene Conversion in Metathesis @ 400° C.

| Run No. | Total Minutes on Stream | Injected Pulses of 1,3-Butadiene @ Minutes on Stream | % Propylene Conversion |
|---|---|---|---|
| | | 123 | |
| | 128 | | 18.9 |
| | | 143 | |
| | 148 | | 20.7 |
| | | 168 | |
| | 169 | | 23.7 |
| | 189 | | 22.8 |

[a]CO activated catalyst.

Referring to the results in run 25 of Table XIX, it is evident that pulses of butadiene to the WO$_3$.SiO$_2$ catalyst failed to cause dramatic increases in % propylene conversion in a typical metathesis operation. For example, pulses of butadiene at 123, 143 and 168 minutes resulted in propylene conversions on the order of 19 to 24% which are not significantly different from propylene conversions in untreated, but representatively active metathesis systems.

TABLE XX

Acetonitrile Pulses to WO$_3$.SiO$_2$ Catalyst
To Enhance Propylene Conversion in Metathesis @ 400° C.

| Run No. | Total Minutes on Stream | Injected Pulses of Acetonitrile @ Minutes on Stream | % Propylene Conversion |
|---|---|---|---|
| 26[a] | 5 | | 4.3 |
| | 25 | | 8.9 |
| | | 35 | |
| | 46 | | 6.7 |
| | 66 | | 10.1 |
| | | 86 | |
| | 87 | | 7.2 |
| | 108 | | 9.6 |
| | 129 | | 12 |
| 27[b] | 5 | | 4.4 |
| | 25 | | 8.7 |
| | | 26* | |
| | | 28** | |
| | 46 | | 7.6 |
| | 66 | | 10.8 |
| | 87 | | 12.9 |

*0.12 g CH$_3$C≡N was added.
**0.24 g CH$_3$C≡N was added.
[a]CO activated catalyst.
[b]No CO activation of catalyst; a 0.1 g pulse of acetonitrile was introduced into the catalyst bed before any propylene feed.

Referring to the results of runs 26 and 27 in Table XX, it is evident that the introduction of acetonitrile into the WO$_3$.SiO$_2$ catalyst bed either prior to the injection of propylene feed or pulsed into the propylene feed elicited no significant increase in propylene conversion for the metathesis operation. The levels of conversion remained significantly lower than observed in typical metathesis runs carried out in the absence of additives containing multiple bonds.

EXAMPLE V

This example describes duplicate runs in which the alkyne (1-hexyne) was pulsed into the propylene feed which was passed through a mixed bed catalyst of MgO and WO$_3$.SiO$_2$. In a typical run, approximately 1.5 g of MgO was intimately mixed with about 0.5 g of WO$_3$.SiO$_2$ (ca. 6 wt % WO$_3$). Results are summarized in Table XXI.

TABLE XXI

1-Hexyne Pulses to Mixed Bed
MgO + WO$_3$.SiO$_2$ Catalyst To Enhance Propylene Conversion @ 275° C.

| Run No. | Total Minutes on Stream | Injected Pulses of 1-Hexyne @ Minutes on Stream | % Propylene Conversion |
|---|---|---|---|
| 28[a] | 5 | | 30.5 |
| | 25 | | 35.8 |
| | 46 | | 36.7 |
| | | 56 | |
| | 66 | | 34.5 |
| | 87 | | 31.8 |
| | | 97 | |
| | 107 | | 27.2 |
| | 126 | | 25.3 |
| 29[b] | 5 | | 37.3 |
| | 25 | | 39.6 |
| | 46 | | 40.1 |
| | 66 | | 40.2 |
| | | 80 | |
| | 87 | | 40.8 |
| | 107 | | 38.6 |
| | | 117 | |
| | 128 | | 34 |
| | 149 | | 31.7 |
| | 169 | | 30.9 |
| | | 181 | |
| | 190 | | 22.5 |

[a]CO activated catalyst.
[b]Duplicate of run 28[a].

Referring to the results of the duplicate runs 28 and 29 in Table XXI, pulsed additions of 1-hexyne to the propylene feed did not result in higher propylene conversion in systems using mixed bed catalyst of MgO and WO$_3$.SiO$_2$ at 275° C. Both runs involved the use of CO activated catalysts.

In run 28 the 1-hexyne pulses at 56 and 97 minutes were followed by lower levels in propylene conversions, respectively, at 87 minutes and 126 minutes. In run 29, e.g., similar depressions in propylene conversions were evident at 107 minutes and 169 minutes after 1-hexyne pulses were introduced, respectively at 80 minutes and 117 minutes.

EXAMPLE VI

This example describes a run in which butene-1 was contacted with the WO$_3$.SiO$_2$ catalyst under metathesis conditions. Pulses of 1-hexyne were used to establish the effect of added alkyne on the level of butene conversion. Results are summarized in Table XXII.

TABLE XXII

1-Hexyne Pulses To Enhance
Butene Conversion Over WO$_3$.SiO$_2$

| Run No. | Total Minutes on Stream | Injected Pulses of 1-Hexyne @ Minutes on Stream | % Propylene Conversion |
|---|---|---|---|
| 30[a] | 5 | | 0.3 |
| | 35 | | 0.3 |
| | | 50 | |
| | 66 | | 0.8 |
| | 96 | | 2 |
| | 127 | | 0.5 |
| | 157 | | 0.7 |
| | 188 | | 0.8 |
| | 210* | | |
| | 218 | | 16.6 |
| | 249 | | 20.7 |
| | 279 | | 21.4 |
| | | 294** | |
| | 310 | | 19.5 |

TABLE XXII-continued

1-Hexyne Pulses To Enhance
Butene Conversion Over $WO_3.SiO_2$

| Run No. | Total Minutes on Stream | Injected Pulses of 1-Hexyne @ Minutes on Stream | % Propylene Conversion |
|---|---|---|---|
|  | 341 |  | 19 |

$^a$Catalyst was activated with CO.
*At 210 minutes, the reactor temperature was increased from 275° C. to 400° C.
**A pulse of 0.11 g 1-hexyne was introduced into the butene-1 feed.

Referring to the results in run 30 of Table XXII, it is evident that the butene-1 metathesis reaction at 275° C. over the $WO_3.SiO_2$ catalyst was quite sluggish as % conversion was generally less than 1% over a period of about 188 minutes. The temperature was increased to 400° C. after 210 minutes and conversion increased to 16.6% and then to as high as 21.4 at 279 minutes due to a thermal effect.

In regard to using 1-hexyne pulses to enhance butene conversion, one 0.12 g pulse of 1-hexyne was introduced at 50 minutes (275° C.) and a second pulse (0.11 g 1-hexyne) was introduced at 294 minutes (400° C.). After the first pulse, conversion more than doubled from 0.3% to 0.8% and after the second pulse, conversion remained about the same, changing from 21.4% to 19.5%.

The examples have been provided merely to illustrate the practice of my invention and should not be read so as to limit the scope of my invention or the appended claims in any way. Reasonable variations and modifications, not departing from the essence and spirit of my invention are contemplated to be within the scope of patent protection desired and sought.

I claim:

1. In a disproportionation process which comprises contacting at least one olefin from the group consisting of:
   acyclic mono- and polyenes having at least 3 up to 10 carbon atoms per molecule, and cycloalkyl and aryl derivatives thereof;
   cyclic mono- and polyenes having at least 4 up to 10 carbon atoms per molecule, and alkyl and aryl derivatives thereof;
   mixtures of two or more of the above olefins; and
   mixtures of ethylene with one or more of the above olefins capable of undergoing disproportionation with a tungsten oxide on silica disproportionation catalyst system under disproportionation conditions, the improvement comprising contacting said catalyst with an activating amount of at least one alkyne conforming to the formula:

wherein each R is independently H or a $C_1$-$C_6$ carbon radical per mole of tungsten oxide.

2. A process in accordance with claim 1 wherein said alkyne is selected from the group consisting of:
   acetylene,
   propyne,
   2-butyne,
   1-pentyne,
   2-pentyne,
   1-hexyne,
   3-hexyne, and
   phenylacetylene.

3. A process in accordance with claim 1 wherein said disproportionation catalyst system is contacted with said alkyne by intermittent pulsed additions mixed with or concurrent with the olefin feed.

4. A process in accordance with claim 3 wherein said pulsed addition comprises adding about 0.1 to 20 moles of alkyne per mole of tungsten oxide per pulse.

5. A process in accordance with claim 3 wherein said disproportionation catalyst is associated with magnesium oxide.

6. A process in accordance with claim 5 wherein said alkyne is provided by the isomerization in the presence of said magnesium oxide of at least one allene having the formula:

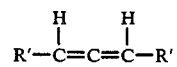

wherein each R' is independently H or a $C_1$-$C_6$ carbon radical.

7. A process in accordance with claim 1 wherein said disproportionation catalyst system is contacted with said alkyne prior to introduction of the olefin feed.

8. A process in accordance with claim 7 wherein said alkyne is introduced in an amount ranging from 0.1 to 20 moles of alkyne per mole of tungsten oxide.

9. A process in accordance with claim 7 wherein said disproportionation catalyst system is associated with magnesium oxide.

10. A process in accordance with claim 9 wherein said alkyne is provided by the isomerization in the presence of said magnesium oxide of at least one allene having the formula:

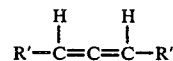

wherein each R' is independently H or a $C_1$-$C_6$ carbon radical.

11. A process in accordance with claim 1 where said disproportionation catalyst system is selected from the group consisting of:
   $WO_3.SiO_2/R_4Sn$,
   $AgO.WO_3.SiO_2$,
   $OsO_4.WO_3.SiO_2$,
   $WO_3.SiO_2/NbTe$,
   $WO_3.SiO_2/MoTe_2$, and
   $WO_3.SiO_2/MgO$.

* * * * *